United States Patent
Damadian et al.

(10) Patent No.: US 10,679,365 B1
(45) Date of Patent: Jun. 9, 2020

(54) METHOD OF CORRELATING A SLICE PROFILE

(75) Inventors: Raymond V. Damadian, Woodbury, NY (US); Robert Viel, Port Washington, NY (US); Robert Wolf, Medford, NY (US); Michael Boitano, Smithtown, NY (US)

(73) Assignee: Fonar Corporation, Melville, NY (US)

( * ) Notice: Subject to any disclaimer, the term of this patent is extended or adjusted under 35 U.S.C. 154(b) by 476 days.

(21) Appl. No.: 13/303,779

(22) Filed: Nov. 23, 2011

Related U.S. Application Data

(60) Provisional application No. 61/416,984, filed on Nov. 24, 2010.

(51) Int. Cl.
| | |
|---|---|
| G06T 7/38 | (2017.01) |
| A61B 5/055 | (2006.01) |
| G06T 7/32 | (2017.01) |
| A61B 5/00 | (2006.01) |

(52) U.S. Cl.
CPC .......... *G06T 7/38* (2017.01); *A61B 5/055* (2013.01); *A61B 5/7425* (2013.01); *G06T 7/32* (2017.01); *G06T 2207/10088* (2013.01); *G06T 2207/20108* (2013.01)

(58) Field of Classification Search
CPC ..... A61B 5/055; A61B 5/0555; A61B 5/7425; A61B 6/5229; G06T 2207/10072; G06T 2207/10088; G06T 2207/20108; G06T 7/30; G06T 7/32; G06T 7/38
See application file for complete search history.

(56) References Cited

U.S. PATENT DOCUMENTS

| | | | |
|---|---|---|---|
| 4,734,646 A | 3/1988 | Shenoy et al. | |
| 4,871,966 A | 10/1989 | Smith et al. | |
| 5,438,263 A | 8/1995 | Dworkin et al. | |
| 5,946,425 A * | 8/1999 | Bove, Jr. .............. | G06T 7/38 |
| | | | 382/128 |
| 6,801,037 B1 | 10/2004 | Zhang | |
| 6,894,707 B2 * | 5/2005 | Nemoto .............. | A61B 6/032 |
| | | | 345/184 |

(Continued)

OTHER PUBLICATIONS

Jinkins et al., "Upright, weight-bearing, dynamic-kinetic MRI of the spine: initial results", Sep. 2005, European Radiology, vol. 15, iss. 9, p. 1815-1825.*

(Continued)

*Primary Examiner* — Vincent Rudolph
*Assistant Examiner* — Timothy Choi
(74) *Attorney, Agent, or Firm* — Lerner, David, Littenberg, Krumholz & Mentlik, LLP

(57) ABSTRACT

A method and system for correlating slice profiles associated with a series of magnetic resonance images taken at a plurality of positions. The method comprises first positioning a patient in a first position in the imaging volume of the magnet. A scout scan is then acquired. Selection is then made of an anatomical landmark in the scout scan, which will be referred to as an anatomical fiducial. A particular slice, typically one of a stack of slices to be acquired in a subsequent scan, is selected and precisely positioned at the location of the anatomical fiducial in the scout scan. Following completion of the scan, the patient may be repositioned, necessitating a new scout scan to set up parameters for a second scan.

9 Claims, 9 Drawing Sheets

(56) References Cited

U.S. PATENT DOCUMENTS

| | | | |
|---|---|---|---|
| 7,372,988 B2* | 5/2008 | Yoakum-Stover | G06T 7/0012 |
| | | | 128/920 |
| 7,557,576 B1 | 7/2009 | Morrone | |
| 8,049,498 B1 | 11/2011 | Morrone | |
| 8,401,612 B1* | 3/2013 | Chu et al. | 600/410 |
| 2004/0024303 A1* | 2/2004 | Banks et al. | 600/407 |
| 2004/0204644 A1* | 10/2004 | Tsougarakis et al. | 600/410 |
| 2005/0169507 A1* | 8/2005 | Kreeger | G06T 7/0012 |
| | | | 382/128 |
| 2006/0100502 A1* | 5/2006 | Chen | A61B 5/02007 |
| | | | 600/419 |
| 2007/0014456 A1* | 1/2007 | Ramamurthy | G06T 7/0012 |
| | | | 382/128 |
| 2008/0063301 A1* | 3/2008 | Bogoni | G06T 7/33 |
| | | | 382/294 |
| 2009/0240137 A1* | 9/2009 | Rosa | 600/411 |

OTHER PUBLICATIONS

Pekar et al., "Automated Planning of Scan Geometries in Spine MRI Scans", Nov. 2, 2007, Medical Image Computing and Computer-Assisted Intervention—MICCAI 2007, vol. 4791, p. 601-608.*

Mauer et al., "Registration of 3D Images Using Weighted Geometrical Features", Dec. 1996, IEEE, IEEE Transactions on Medical Imaging, vol. 15, No. 6, p. 836-849. (Year: 1996).*

* cited by examiner

METHOD OF CORRELATING A SLICE PROFILE

CROSS-REFERENCE TO RELATED APPLICATIONS

The present application claims the benefit of the filing date of U.S. Provisional Patent Application No. 61/416,984 filed Nov. 24, 2010, the disclosure of which is hereby incorporated herein by reference.

BACKGROUND

Magnetic resonance imaging ("MRI") offers numerous advantages over other imaging techniques. MRI does not expose either the patient or medical personnel to X-rays and offers important safety advantages. Also, MRI can obtain images of soft tissues within the body which are not readily visualized using other imaging techniques. In magnetic resonance imaging, an object to be imaged as, for example, a body of a human subject is exposed to a strong, substantially constant static magnetic field. The static magnetic field causes the spin vectors of certain atomic nuclei within the body to randomly rotate or "precess" around an axis parallel to the direction of the static magnetic field. Radio frequency excitation energy is applied to the body, and this energy causes the nuclei to "precess" in phase and in an excited state. As the precessing atomic nuclei relax, weak radio frequency signals are emitted; such radio frequency signals are referred to herein as magnetic resonance signals.

Different tissues produce different signal characteristics. Tissues having a high density of nuclei will produce stronger signals than tissues with a low density of such nuclei. Furthermore, relatively small gradients in the magnetic field are superimposed on the static magnetic field at various times during the process, so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

Conventionally, MRI machines require that a patient lie in a horizontal position and then be advanced into a tubular enclosure within a super-conducting solenoidal magnet used to generate the static magnetic field. Ferromagnetic frame magnets having horizontal pole axes have been developed, which allow a patient to be imaged in a variety of positions including, for example, upright (sitting or standing), recumbent, Trendelenburg and reverse-Trendelenburg positions.

More specifically, ferromagnetic frame magnets having horizontal pole axes have been disclosed, for example, in commonly assigned U.S. Pat. No. 6,414,490, the disclosures of which are incorporated by reference herein, and U.S. Pat. No. 6,677,753, filed on Nov. 22, 2000, the disclosure of which is also incorporated by reference herein, a magnet having poles spaced apart from one another along a horizontal axis provides a horizontally oriented magnetic field within a patient-receiving gap between the poles. Such a magnet can be used with a patient positioning device including elevation and tilt mechanisms to provide extraordinary versatility in patient positioning. For example, where the patient positioning device includes a bed or similar device for supporting the patient in a supine or recumbent position, the bed can be tilted and/or elevated so as to image the patient in essentially any position between a fully standing position and a fully supine or fully recumbent position, and can be elevated or lowered so that essentially any portion of the patient's anatomy is disposed within the gap in an optimum position for imaging. As further disclosed in the aforesaid patents, the patient positioning device may include additional elements such as a platform, any type of seat, or both, projecting from the bed to support the patient when the bed is tilted towards a standing orientation. Still, other patient supporting devices can be used in place of a bed in a system of this type. Thus, magnets of this type provide extraordinary versatility in imaging.

For example, these systems allow evaluation of the spine in its all of its weight bearing (e.g., neutral, flexion and extension) and recumbent positions. In order to enable proper diagnosis of back pain, for example, it is usually important that a particular area of anatomical interest (e.g., a particular vertebrae) be evaluated in these different positions.

However, in switching from one of these positions to another, the patient is intentionally repositioned in the new position, resulting in a fairly large movement of the anatomy of interest both relative to neighboring anatomy, and relative to the imaging region in the magnet. Furthermore, repositioning a patient from one of the upright positions to the recumbent position, and vice versa, may involve removal of the patient from the imaging volume, and either removal or addition of a seat to the patient positioning bed before repositioning the patient in the imaging volume. Here certainly, the change in the position of the patient's anatomy is rather extreme. These examples illustrate the need to have a method and system, which would help insure alignment of imaging slices from scan to scan in different body positions.

SUMMARY

In one aspect, the present invention is a system and concomitant method for correlating magnetic resonance imaging slice profiles. Correlated slice profile is a magnetic resonance (MR) imaging method to help in tracking and correlation of an anatomical feature of interest in multiple weight-bearing position, through a series of scans. Such a feature visible in a particular slice in a scan could then be monitored in subsequent scans in other weight-bearing body positions, in order to facilitate diagnosis.

One example of a potential use for this method is when the position of a patient changes through a course of a study and there is an interest in correlating the slices of a scan in multiple body positions across several scans, in order to more completely evaluate the patient's pathology. The position of a patient may change due to involuntary or uncontrolled movement between scans in different positions. The position of a patient may be intentionally changed in order to determine the effect of a fully weight-loaded body position on the anatomic structure or function of a body part (e.g., intervertebral disc, spinal cord, cerebrospinal fluid flow). In scanners that are capable of scanning patients in a variety of positions, including recumbent, upright neutral, upright flexion, and upright extension, additional advantages may be achieved. The three latter positions are weight-bearing and are preferably performed with the patient seated.

The correlated slice profile method involves first positioning a patient in a first position in the imaging volume of the magnet. A scout scan is then acquired. Selection is then made of an anatomical landmark in the scout scan (e.g., the spinal cord), which will be referred to as an anatomical fiducial. A particular slice, typically one of a stack of slices to be acquired in a subsequent scan, is selected and precisely positioned at the location of the anatomical fiducial in the scout scan. For the purposes of illustration herein, this designated slice will be #8, from a series of 15 slices.

Following completion of the scan, the patient may be repositioned, necessitating a new scout scan to set up parameters for a second scan. The anatomical fiducial is identified on this second scout scan (e.g., the spinal cord) and the same designated slice, #8, as in the first scan, is positioned on the anatomical fiducial. The second scan is then acquired. Positioning of the central slice, slice #8, as in the first scan, is positioned on the anatomical fiducial for each body position assures that the remaining parallel slices of the scan are the same anatomy in all body positions. This method will then allow direct comparison of the anatomical structures from the two scans, even though the position of the patient may be very different between the first and second scans. The image slices are said to be correlated.

In another aspect, a method for correlating images obtained from a magnetic resonance imaging scan is provided. The method preferably comprises acquiring a first scout scan having one or more image slices of a patient in a first position; associating a first image slice from among the one or more image slices with an anatomical landmark; acquiring a first scan of the patient in the first position with the first image slice positioned at the anatomical landmark; acquiring a second scout scan having one or more image slices of a patient in a second position; associating a second image slice from among the one or more of image slices with the landmark; acquiring a second scan of the patient in the second position with the second image slice positioned at the anatomical landmark; and displaying a plurality of images including at least the first and second image slices from the first scan and second scans adjacent to each other such that the anatomical landmark in the first and second positions is correlated.

In another aspect, a system for correlating magnetic resonance images is provided. The system preferably comprises a magnetic resonance imaging apparatus for acquiring magnetic resonance images from a patient in at least two positions; a computer coupled to the magnetic resonance imaging apparatus, the computer having a memory for storing instructions and a processor for executing the instructions, the instructions causing the processor to: acquire a first scout scan having a first plurality of image slices of a patient in a first position; identify a first image slice associated with an anatomical landmark from among the first plurality of image slices; acquire a first scan of the patient in the first position with the first image slice positioned at the anatomical landmark; acquire a second scout scan having a second plurality of image slices of a patient in a second position; identify a second image slice from among the second plurality of image slices, the second image slice associated with the anatomical landmark; acquire a second scan of the patient in the second position with the second image slice positioned at the anatomical landmark; and display a plurality of images including at least the first image slice from the first scan and the second image slice from the second scan adjacent to each other such that the anatomical landmark in the first and second positions is correlated.

DETAILED DESCRIPTION

Figure 1:
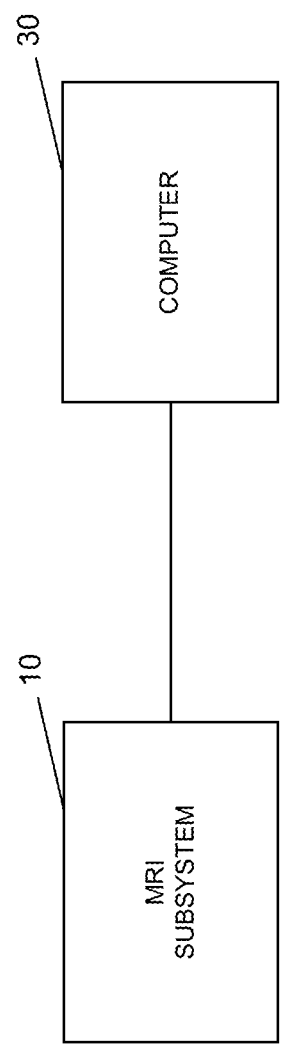
FIG. 1 illustratively depicts a magnetic resonance imaging system in accordance with an aspect of the present invention.

Turning now to FIG. 1, there is shown a magnetic resonance imaging ("MRI") system 1 in accordance with an aspect of the present invention. The system includes an MRI subsystem 10 and computer 30. The MRI subsystem 10 operates under the control of computer 30. The subsystem 10 and computer 30 may be connected over a network or via a direct connection. The networks may include a local area network running Ethernet or other network protocols, WiFi or any other type of network the enables communications between two devices. The computer 30 is operable to control the subsystem 10 in acquiring images, including the pulse sequences, image acquisition and reconstruction.

In general, the subsystem preferably allows patient to be imaged in positions other than just the recumbent position. For example, FIG. 2 of the current application shows a sectional view of an MRI magnet subsystem 100 that can be used in accordance with a preferred embodiment of the present application. MRI magnet subsystem 100 includes a magnet having a ferromagnetic frame 102, a flux generating means 104 as is described in further detail below, and a patient handling system 106. The ferromagnetic frame 102 includes a first side wall 108 and a second side wall (not shown). The side walls extend vertically. For purposes of clarity, FIG. 2 does not show the second side wall or any of its associated structures (though it should be understood that the second side wall will include elements similar to those contained in the first side wall 108). The ferromagnetic frame 102 also includes a top flux return structure 112 and a bottom flux return structure 114. The top flux return structure 112 may include two columns 116 and 118. Between these two columns, a top opening 120 is defined. Similarly, the bottom flux return structure 114 may include two columns 122 and 124 that together define a bottom opening 126. Thus, the side walls and the flux return members 112 and 114 form a rectilinear structure, with the top flux return structure 112 constituting the top wall of the rectilinear structure, the bottom flux return structure 114 constituting the bottom wall of the rectilinear structure and the side walls forming the side walls of the rectilinear structure. The frame 102 of the rectilinear structure defines a front patient opening 128 on one side of the frame 102 and a similar back patient opening 130 on the opposite side of the frame 102. The ferromagnetic frame 102 further includes a first magnetic pole 132 and a second magnetic pole (not shown, but horizontally displaced opposite the first magnetic pole 132). The first magnetic pole 132 extends from the first side wall 108 towards the second side wall and the second magnetic pole extends from the second side wall towards the first side wall 108. The magnetic poles are generally cylindrical and are coaxial with one another on a common horizontal polar axis 136. Between the magnetic poles is a gap 131, also referred to as the patient-receiving space, of the magnet. The gap or patient-receiving space 131 is accessed by the front patient opening 128, the back patient opening 130, the top opening 120 or the bottom opening 126.

The flux generating means 104 includes a first electromagnetic coil assembly 138 which surrounds the first magnetic pole 132, and a second electromagnet coil assembly, which surrounds the second magnetic pole (not shown but comparable to the first electromagnetic coil assembly 138). These electromagnetic coil assemblies 138 and 140 may be either resistive or superconductive.

The patient handling system 106 is capable of three degrees or axes of motion. The patient handling system 106 may be termed a stand-up patient handling system, although the patient handling system 106 is not limited to standing position applications. The patient handling system 106 includes a carriage 142 mounted on rails 144. The carriage 142 may move linearly back and forth along the rails 144. The rails 144 typically do not block the bottom open space 126.

Figure 2:
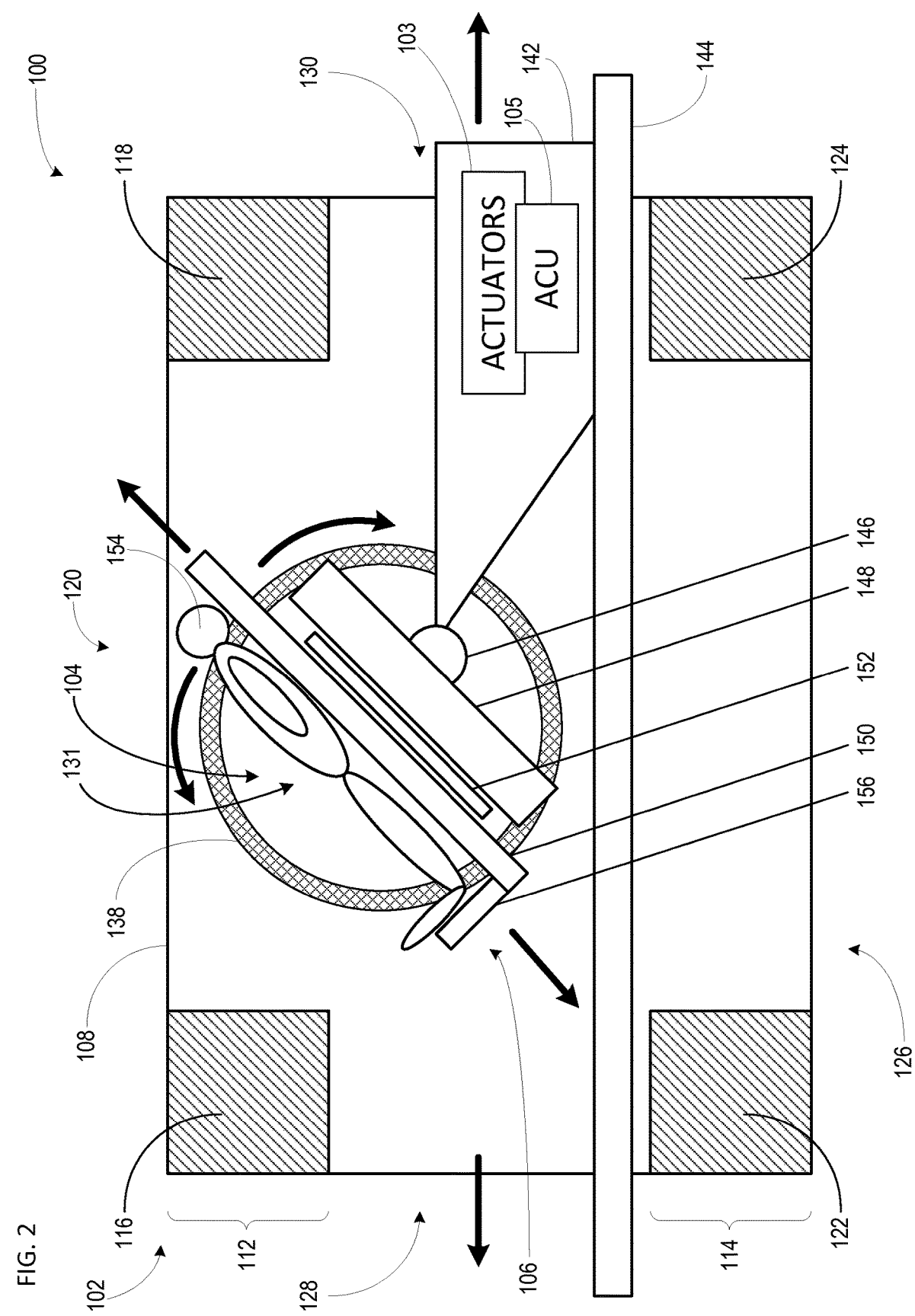
FIG. 2 illustratively depicts a magnetic resonance imaging subsystem in accordance with an aspect of the present invention.

A generally horizontal pivot axis 146 is mounted on carriage 142. An elevator frame 148 is mounted to the pivot axis 146. The carriage 142 is operable to rotate the elevator frame 148 about the pivot axis 146. A patient support 150 is mounted on the elevator frame 148. The patient support 150 may be moved linearly along the elevator frame 148 by an actuator 152. Thus, a patient 154 can be positioned with a total of three degrees of freedom, or along three axes of movement or motion. Specifically, the patient handling system 106 can move a patient 154 in two linear directions and also rotate patient 154 around an axis. The solid black arrows of FIG. 2 show the three axes of movement possible with the patient handling system 106. Note that often the rails 108 are mounted such that portions of patient 154 may be positioned below the rails through bottom open space 126.

Often, a foot rest 156 may be used in order to support a patient in a standing position. Given the wide variety of positions possible with the patient handling system 108, many other such supports may be implemented, such as chair seats or straps.

The patient handling system 106 incorporates one or more actuators 103 and an actuation control unit 105. Actuators 103 may be conventional electrical, electromechanical, pneumatic, hydraulic or other devices capable of imparting the desired motion to the elements of the patient handling system. For example, the actuators may include elements such as conventional stepper motors or other conventional electric motors linked to the elements of the patient handling system 106. The actuator control unit 105 may incorporate a conventional programmable controller, microprocessor, or computer with appropriate input and output interfaces. The actuation control unit 105 is linked to a control computer (such as computer 30) and to the manual controls which regulate the patient handling system. The actuation control unit may be mounted in proximity to the actuators 103 as, for example, on carriage 142.

Figure 3:
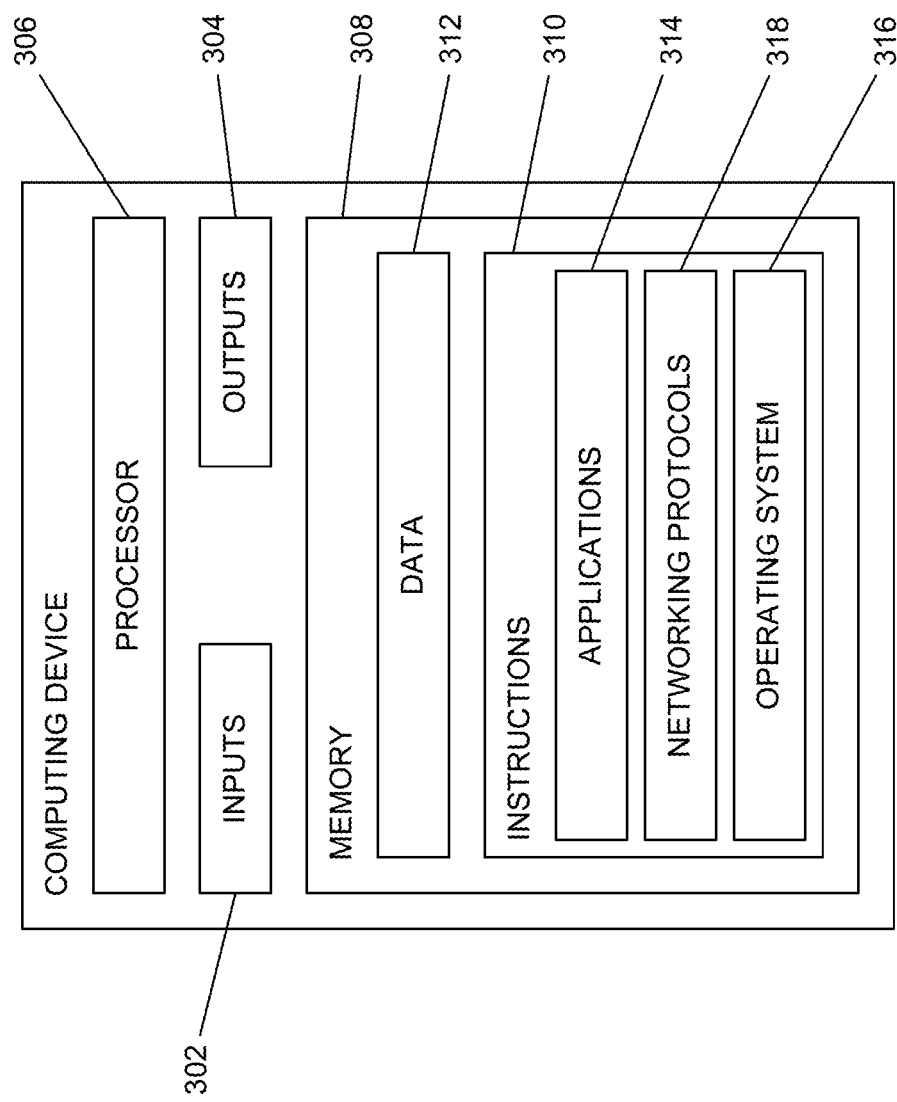
FIG. 3 illustrates an apparatus for implementing the computer of the system disclosed in FIG. 1.

FIG. 3 shows an apparatus 300 for implementing the computer 30 depicted in the system 1 presented in FIG. 1. As seen therein, apparatus 300 illustrates one configuration of a computing device that may be used to control the MRI subsystem in accordance with method steps described below.

The apparatus 300 may include, for example, one or more user inputs 302 such as a keyboard and mouse and/or other types of input devices such as pen-inputs, joysticks, buttons, touch screens, etc., as well as a display 304, which could include, for instance, a CRT, LCD, plasma screen monitor, TV, projector, etc. As shown, apparatus 300 further contains a processor 306, and memory or computer readable medium 308.

Memory 308 stores information accessible by processor 306, including instructions 310 that may be executed by the processor 306 and data 312 that may be retrieved, manipulated or stored by the processor. The memory 308 may be of any type capable of storing information accessible by the processor, such as a hard-drive, ROM, RAM, CD-ROM, DVD, Blu-Ray disk, flash memories, write-capable or read-only memories. The processor 306 may comprise any number of well known processors, such as processors from Intel Corporation and Advanced Micro Devices. Alternatively, the processor 306 may be a dedicated controller for executing operations, such as an ASIC.

The instructions 310 may comprise any set of instructions to be executed directly (such as machine code) or indirectly (such as scripts) by the processor. In that regard, the terms "instructions," "applications" and "programs" are used interchangeably herein. The instructions may be stored in any computer language or format, such as in executable/object code or modules of source code.

Data 312 may be retrieved, stored or modified by processor 306 in accordance with the instructions 310. The data may be stored as a collection of data. For instance, although the invention is not limited by any particular data structure, the data may be stored in computer registers, in a relational database as a table having a plurality of different fields and records, XML documents, or flat files.

The data may also be formatted in any computer readable format such as, but not limited to, binary values, ASCII etc. Similarly, the data may include images stored in a variety of formats. Moreover, the data may include any information sufficient to identify the relevant information, such as descriptive text, proprietary codes, pointers, references to data stored in other memories (including other locations in a network) or information which is used by a function to calculate the relevant data.

Although the processor 306 and memory 308 are functionally illustrated in FIG. 3 as being within the same block, it will be understood that the processor and memory may actually comprise multiple processors and memories that may or may not be stored within the same physical housing or location. For example, some or all of the instructions and data may be stored on a computer-readable removable recording medium such as a CD-ROM, DVD or Blu-Ray disk. Alternatively, such information may be stored within a read-only computer chip. Some or all of the instructions and data may be stored in a location physically remote from, yet still accessible by, the processor. Similarly, the processor may actually comprise a collection of processors which may or may not operate in parallel. Data may be distributed and stored across multiple memories 308 such as hard drives, data centers, server farms or the like.

In addition, the memory 308 in apparatus 300 may include one or more applications or programs 314 adapted to provide the any of the functions described with respect to the computer 30 and in accordance with the various aspects of the invention discussed above and below. Each device may include and execute specific instructions or applications, desirably under management of the processor 306 in conjunction with an operating system 316 and networking protocols instructions 318 to provide the functionality described above.

Figure 4:
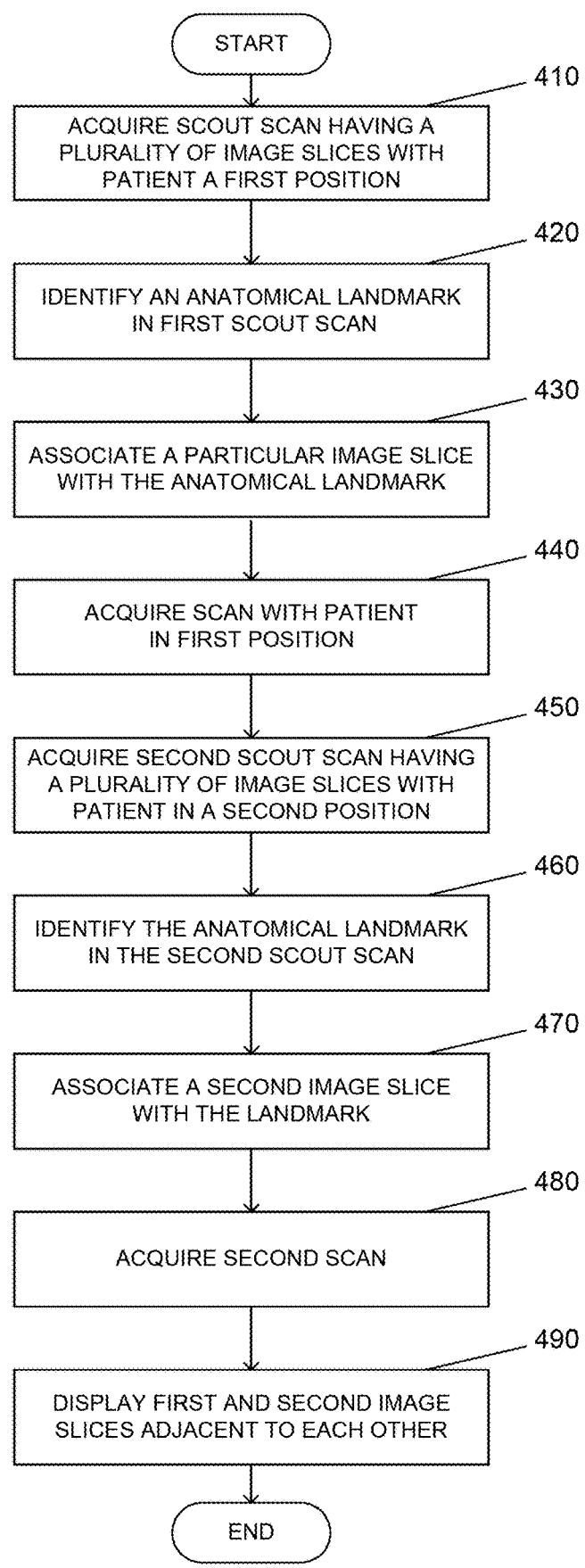
FIG. 4 illustrates the steps of a method in accordance with an aspect of the present invention.

Turning now to FIG. 4, there is depicted a process 400 for obtaining a correlated slice profile in accordance with an aspect of the present invention. The method comprises acquiring a scout scan, step 410, of portion of a patient's anatomy. A scout scan typically includes a plurality of image slices, each image slice being associated with a particular portion of the anatomy of interest. For example, a scout scan of the lumbar spine may result in 20 or more images splice, some of which are preferably associated with a particular lumbar disc, e.g., L3. Using the scout scan, an anatomical landmark is identified in the scout scan, step 420, for further evaluation. Next one of the image slices is then associated with the anatomical landmark, step 430. This may be done by positioning the 8$^{th}$ slice, for example, on the L3 disc. With the target slice positioned on the anatomical landmark, a scan is then acquired, step 440.

Next, the patient is then repositioned. A scout scan is then acquired with the patient in this second position, step 450. This scout will also preferably include a plurality of image slices. The anatomical landmark or fiducial is then identified from among these slices, step 460. An image slice, preferably the 8$^{th}$ slice, is then associated with or positioned on the landmark, step 470, and another scan is acquired, step 480. Next, a comparison of images slices associated with or positioned on the landmark during the first and second scans provides a correlation between the slice profiles, step 490. In other words, by displaying these image slices adjacent to each other, changes in the anatomical landmark as a result of the change in position may be easily determined.

In the foregoing, in the first and second scans the same scout slice was associated with the anatomical landmark. Using the same slice, e.g., 8$^{th}$ slice, is not critical. What is important is that a particular slice is associated with the same landmark. In this way, as explained below, the images from the different scans can be panned and aligned so that the landmark is shown side-by-side in the different scan positions. In addition, FIG. 4 is described with respect to two scans, but the method be extended to additional scans by placing the patient in additional positions.

The method may be applied to any number of scans in a series or study in order to compensate for changes in anatomical position and location which can occur due to movement or repositioning. As related to the example given herein, a study may include scanning a patient in four very different positions, viz., recumbent, upright neutral, upright flexion, and upright extension. The anatomical fiducial alignment procedure of the correlated slice profile (CSP) scanning method would enable the medical practitioner to directly compare the same slices obtained in different body positions with each other. This would enable the practitioner to make a more complete evaluation of the full extent of the variation of a patient's anatomic pathology with position in order to optimize the surgical procedure or medical treatment being prescribed.

Figure 5:
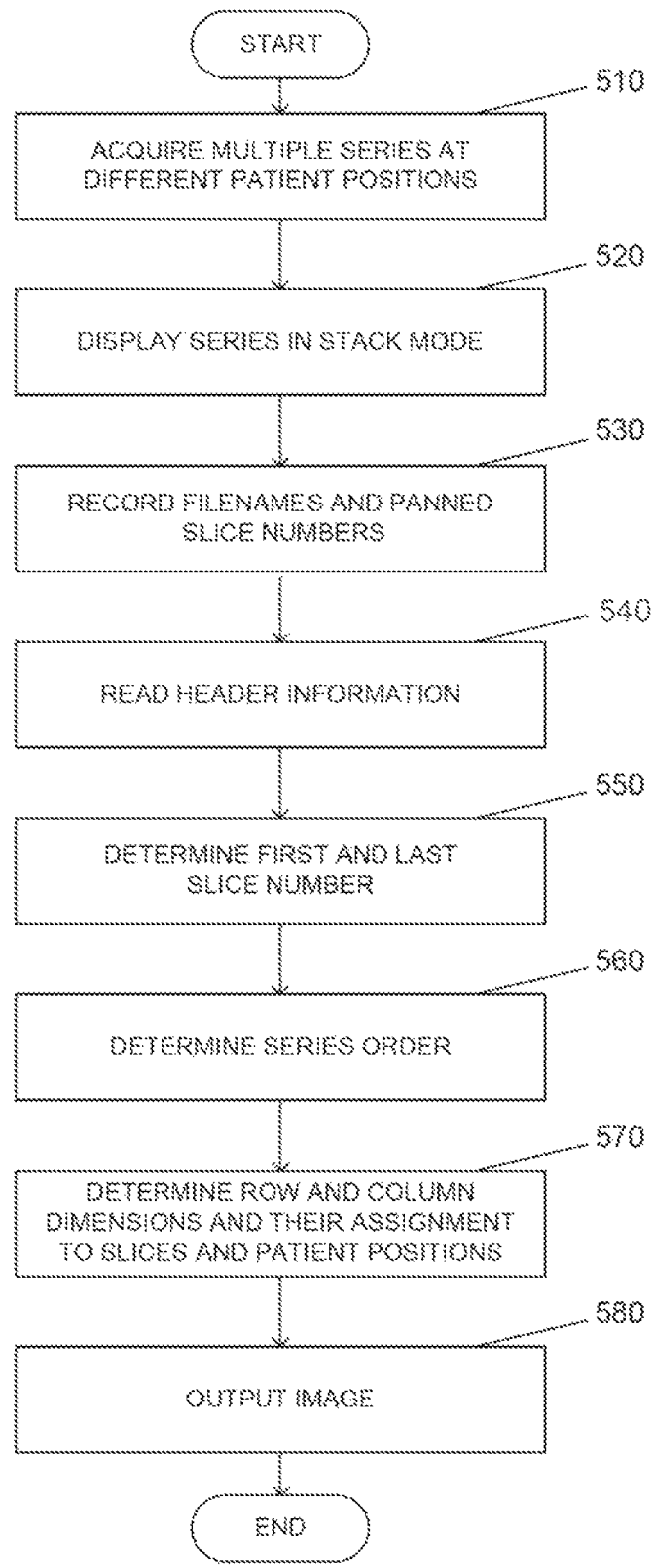
FIG. 5 illustrates the steps of a method in accordance with an aspect of the present invention.

FIG. 5 shows a process 500 for also correlating slice profiles in accordance with an additional aspect of the present invention. FIG. 5 is a high level description of the method that was implemented as software instructions stored in a memory and used to operate a processor in accordance with an aspect of the present invention.

At step 510, multiple series of images are acquired at different patient positions, preferably for example recumbent, neutral/sitting, flexion, and/or extension. The slice placement is repositioned prior to each series acquisition to attempt consistent slice positions between the series. In our implementation, each series produces images from equally spaced parallel slice planes with the same slice spacing.

At step 520, each series is displayed in "stack" mode. Stack mode displays one image from each series and allows independent panning through the slices in the same image frame on the screen. Slice panning allows visual correlation of slice positions between the images from each series. Panning and visual correlation compensates for any slice registration errors after the image acquisition.

Figure 6:
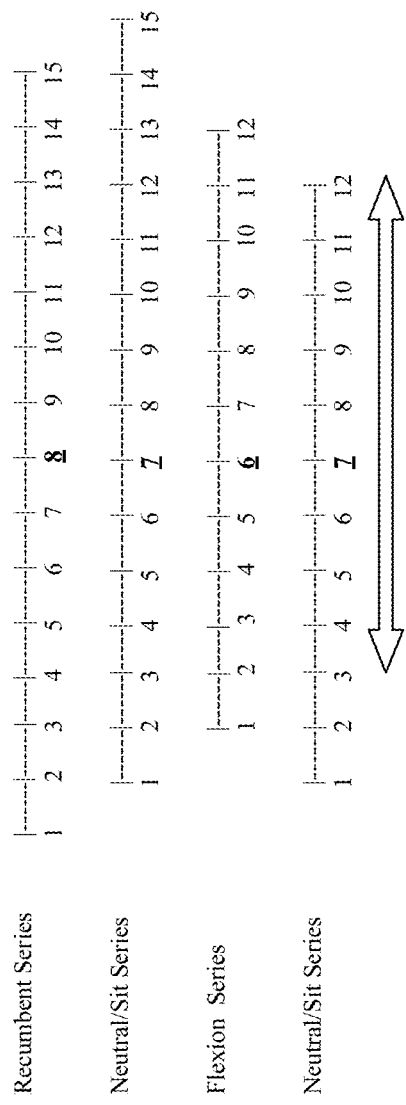
FIG. 6 shows panned slices in a series of slices acquired for different scans.

At step 530, the filenames of each image series are recorded along with the "panned" slice numbers from Step 520. Next, at step 540, the header information from each series is read to obtain the total number of slices in the series and a comment field that identifies the patient position (e.g. "Flex", or "Neutral"). The "panned" slice number and total number of slices are then used, step 550, in the series to determine the first and last slice numbers to output for each series. The stack of slices is modeled for each series as number lines with slices to the left and right of the panned slice. This algorithm allows each series to have a different number of slices and determines maximum number of slices to output with correlated slices from each series. See for example FIG. 6. In FIG. 6, the "panned" slice (8, 7, 6, 7 at for recumbent, neutral/sit, flexion and neutral/sit positions) from each series is shown in bold underlined. Each series may have a different number of slices. The first and last slice output for each series is determined by the minimum number to the left or right of the panned slices.

An algorithm for implementing step 560 in pseudo-code may be implemented as follows:
  a. Initialize LeftSideMin=9999 and RightSideMin=9999
  b. Do the following for each series to determine LeftSideMin and RightSideMin:
    i. LeftSide=PannedSlice−1
    ii. RightSide=SlicesInSeries−PannedSlice
    iii. LeftSideMin=minimum(LeftSideMin, LeftSide)
    iv. RightSideMin=minimum(RightSideMin, RightSide)
  c. Do the following for each series to set the first and last slice numbers to output:
    i. FirstSlice=PannedSlice−LeftSideMin
    ii. LastSlice=PannedSlice+RightSideMin At step 560, the series order is determined from the comments. The preferred order (recumbent, neutral/sitting, flexion, extension) is to place the patient positions with the biggest expected anatomical differences adjacent to each other. A lookup table is used with keywords for each position to find matches in the comment fields read from the headers in step 540.

At step 570, the row and column dimensions and their assignments to slices and patient positions are determined. This may be placed under user control or determined automatically by the number of patient positions acquired. Tradeoffs may exist for the image size and output media requirements. A preferred format is to assign the patient positions to different columns, so they "read" left to right, and assign slices to different rows. Using a 4-row by 4-column format for X-ray size film in portrait orientation results in a slightly smaller frame size than a 4-row by 3-column format. The frame size difference may make it desirable to swap the row and column assignments. The assignment and dimension of the rows and columns may require using "blank" filler images if some of the patient positions were not acquired.

Figure 7:
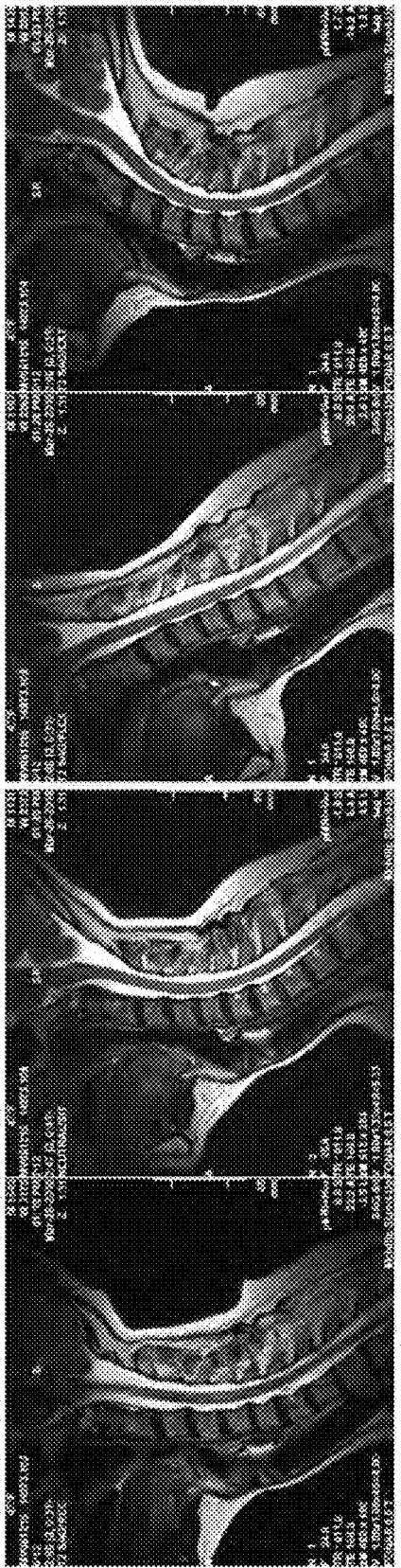
FIG. 7 shows a sample output in accordance with an aspect of the present invention.
Figure 8A:
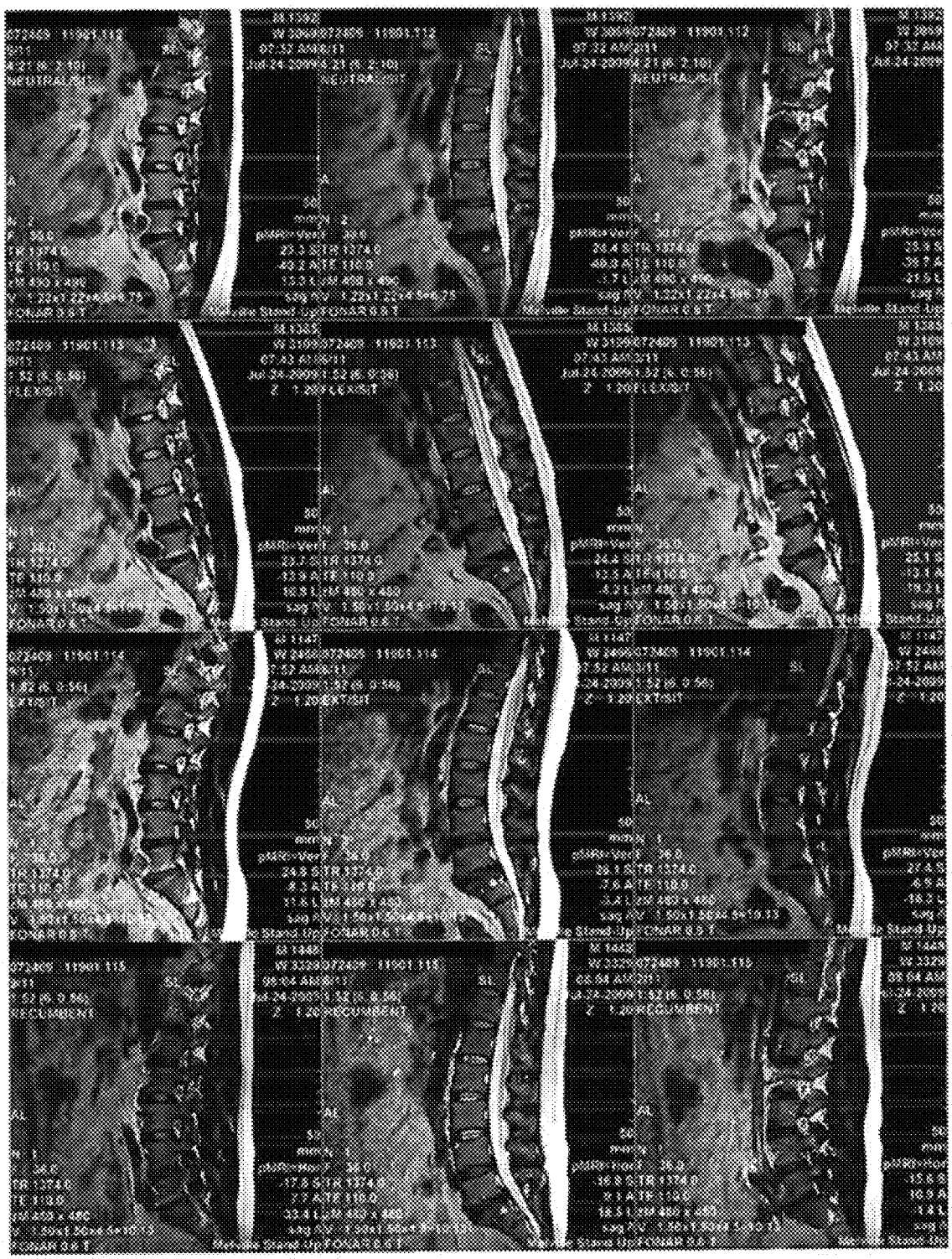
FIGS. 8A and 8B show sample outputs in accordance with an aspect of the present invention.
Figure 8B:
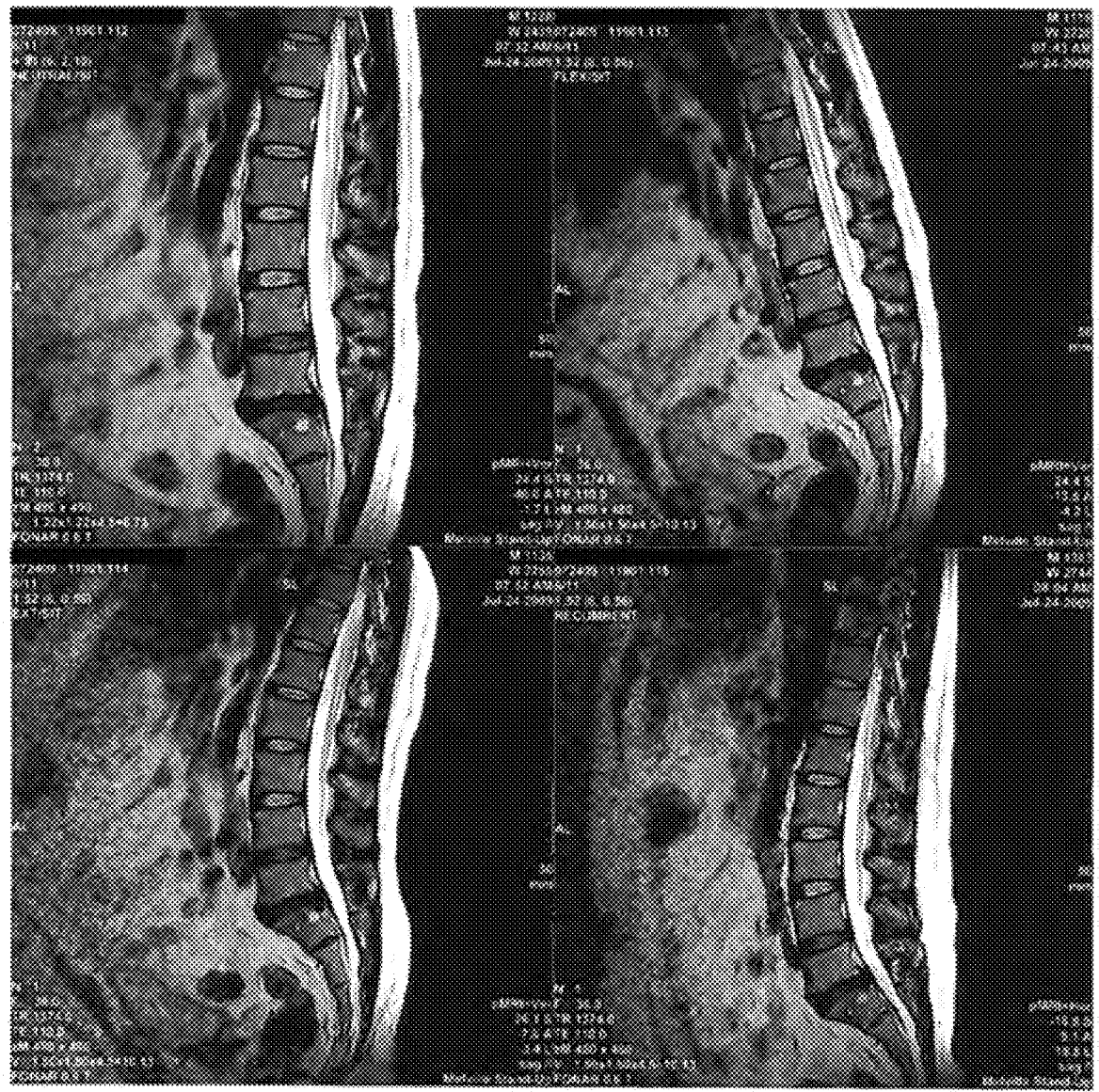

At step 580, each image is transferred in the predetermined order (i.e., the order determined by steps 550, 560, 570) to the output media. Pseudo-code for performing this step may be implemented as follows:
   a. Determine the number of "pages" (or sheets of film)
      iii. ImagesPerPage=Rows*Columns
      iv. TotalImages=NumberOfSeries*(LastSlice−FirstSlice+1)
      v. NumberOfPages=(int) ((TotalImages−1)/ImagesPerPage)+1
   b. For each page
      vi. For each row
         1. For each column
            a. Read selected image pixel data (or blank)
            b. Output pixel data to media FIG. 7 shows a series of correlated images that have been generated in accordance with an aspect of the present invention. As the images show, a particular area of the anatomy is displayed side-by-side allowing for easy diagnosis by a physician. FIGS. 8A and 8B show a second set of correlated images. In FIG. 8A, there is shown in each row three slices from a scan with the patient in the same position for the same anatomical landmark. The images along the column show the same landmark but in different positions. In particular, the first row of FIG. 8A shows the lumbar spine area with the patient in the neutral sitting position. The slice at the center of the row is conceptually slide 7 for the Neutral/Sit series in FIG. 6. The center slide in the second row would conceptually correspond to slide 6 in the flexion series of FIG. 6.

FIG. 8B includes a column from FIG. 8A, e.g., the center column. Alternatively, the images may be displayed as shown in FIG. 7 with additional graphical information showing the position of the patient during the scan.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A method for correlating images obtained from a magnetic resonance imaging scan, comprising:
   acquiring, using a magnetic resonance imaging apparatus capable of acquiring magnetic resonance images from patients in a plurality of positions, a first set of magnetic resonance images of a patient in a first position, the first set of magnetic resonance images comprising a first plurality of image slices with a predetermined slice spacing;
   acquiring, using the magnetic resonance imaging apparatus, a second set of magnetic resonance images of the patient in a second position, the second set of magnetic resonance images comprising a second plurality of image slices with the predetermined slice spacing;
   correlating a first image slice from among the first plurality of images slices having an image of an anatomical landmark with a second image slice from among the second plurality of image slices having an image of the anatomical landmark, in which correlating a first image slice with a second image slice includes modelling the first and second plurality of image slices from each of the first and second sets of magnetic resonance images as numbered lines with slices to the left and right of either the first image slice having the image of the anatomical landmark or the second image slice having the image of the anatomical landmark and in which the first image slice or the second image slice comprises a panned image slice having a panned slice number and the panned slice number and a total number of slices of the first or second set of magnetic resonance images determine a first and last slice number; and
   displaying image slices associated with the first slice number and the last slice number and the plurality of image slices from the first and second set of magnetic resonance images so that the first image slice and second image slice serve as markers by which the first set and second set of magnetic resonance images are aligned relative to each other.

2. The method of claim 1, wherein the first and second positions are selected from the group consisting of a recumbent position, upright neutral position, upright flexion position, and upright extension position.

3. The method of claim 1, wherein the first and second scans are obtained along a plane selected from the group consisting of an sagittal, coronal and axial planes.

4. The method of claim 1, wherein the anatomical landmark is chosen from the group consisting of the intervertebral disc, spinal cord and cerebrospinal fluid.

5. The method of claim 1, wherein the first position or second position comprise a position between a recumbent position and an upright position.

6. The system of claim 1, wherein the panned image is used to correlate slice positions between the first and second set of magnetic resonance images.

7. A system for correlating magnetic resonance images, comprising:
   a magnetic resonance imaging apparatus for acquiring magnetic resonance images from a patient in at least two positions; and
   a computer coupled to the magnetic resonance imaging apparatus, the computer having a memory for storing instructions and a processor for executing the instructions, the instructions causing the processor to:
      acquire a first plurality of image slices of a patient in a first position, the first plurality of image slices having a predetermined slice spacing and a first number of slices;
      acquire a second plurality of image slices of the patient in a second position, the second plurality of image slices having the predetermined slice spacing;
      correlate a first image slice from among the first plurality of images slices having an image of an anatomical landmark with a second image slice from among the second plurality of image slices having an image of the anatomical landmark, in which to correlate a first image slice with a second image slice includes modelling the first and second plurality of image slices from each of the first and second sets of magnetic resonance images as numbered lines with slices to the left and right of either the first image slice having the image of the anatomical landmark or the second image slice having the image of the anatomical landmark and in which the first image slice or the second image slice comprises a panned image slice having a panned slice number and the panned slice number and a total number of slices of the first or second set of magnetic resonance images determine a first and last slice number; and
      display image slices associated with the first slice number and the last slice number and the first and second plurality of image slices so that the first image slice and second image slice serve as markers by which the first and second plurality of image slices are aligned relative to each other when displayed in a stacked mode.

8. The system of claim 7, wherein the first and second positions are selected from the group consisting of a recumbent position, upright neutral position, upright flexion position, and upright extension position.

9. The system of claim 7, wherein the first position or second position comprise a position between a recumbent position and an upright position.

* * * * *